United States Patent [19]
Caro

[11] Patent Number: 6,039,754
[45] Date of Patent: *Mar. 21, 2000

[54] VASCULAR PROSTHESES

[75] Inventor: Colin Caro, London, United Kingdom

[73] Assignee: Imperial College of Science Technology & Medicine, London, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/624,433

[22] PCT Filed: Sep. 16, 1994

[86] PCT No.: PCT/GB94/02023

§ 371 Date: May 28, 1996

§ 102(e) Date: May 28, 1996

[87] PCT Pub. No.: WO95/09585

PCT Pub. Date: Apr. 13, 1995

[30]   Foreign Application Priority Data

Oct. 1, 1993 [GB] United Kingdom ............... 9320288
Jun. 27, 1994 [GB] United Kingdom ............... 9412882

[51] Int. Cl.$^7$ ..................................................... A61F 2/06
[52] U.S. Cl. ................................................ 623/1; 623/12
[58] Field of Search ............................. 623/1, 9, 11, 12; 600/36; 604/8–10

[56]   References Cited

U.S. PATENT DOCUMENTS

| | | | |
|---|---|---|---|
| 4,098,571 | 7/1978 | Miyata et al. | 422/100 |
| 4,225,979 | 10/1980 | Rey et al. | 623/12 |
| 4,313,231 | 2/1982 | Koyamada | |
| 4,345,414 | 8/1982 | Bornat et al. | 623/1 |
| 4,441,215 | 4/1984 | Kaster | 623/1 |
| 4,501,263 | 2/1985 | Harbuck | 623/1 |
| 4,795,465 | 1/1989 | Marten | 623/12 |
| 4,938,740 | 7/1990 | Melbin | 600/36 |
| 5,139,515 | 8/1992 | Robicsek | 623/1 |
| 5,156,619 | 10/1992 | Ehrenfeld | 623/1 |
| 5,236,446 | 8/1993 | Dumon | 623/12 |
| 5,236,447 | 8/1993 | Kubo et al. | 623/12 |
| 5,258,027 | 11/1993 | Berghaus | 623/12 |

FOREIGN PATENT DOCUMENTS

| | | |
|---|---|---|
| 0 503 101 | 9/1992 | European Pat. Off. . |
| 2 666 502 | 3/1992 | France . |
| 93/02637 | 2/1993 | WIPO . |

OTHER PUBLICATIONS

Frazin et al. *Circulation*, "Functional Chiral Asymmetry in Descending Thoracic Aorta," vol. 82, No. 6, Dec. 1990, 1985–1994.

*Primary Examiner*—Mickey Yu
*Assistant Examiner*—Tram A. Nguyen
*Attorney, Agent, or Firm*—Fay, Sharpe, Fagan, Minnich & McKee, LLP

[57]   ABSTRACT

A vascular prosthesis includes a length of generally hollow tubing having openings at both ends thereof. The prosthesis includes at least one curved portion whose curvature extends within three dimensions of two mutually perpendicular planes such as to induce swirl flow in a liquid medium when such medium flows through the curved portion.

19 Claims, 7 Drawing Sheets

FIG. 1
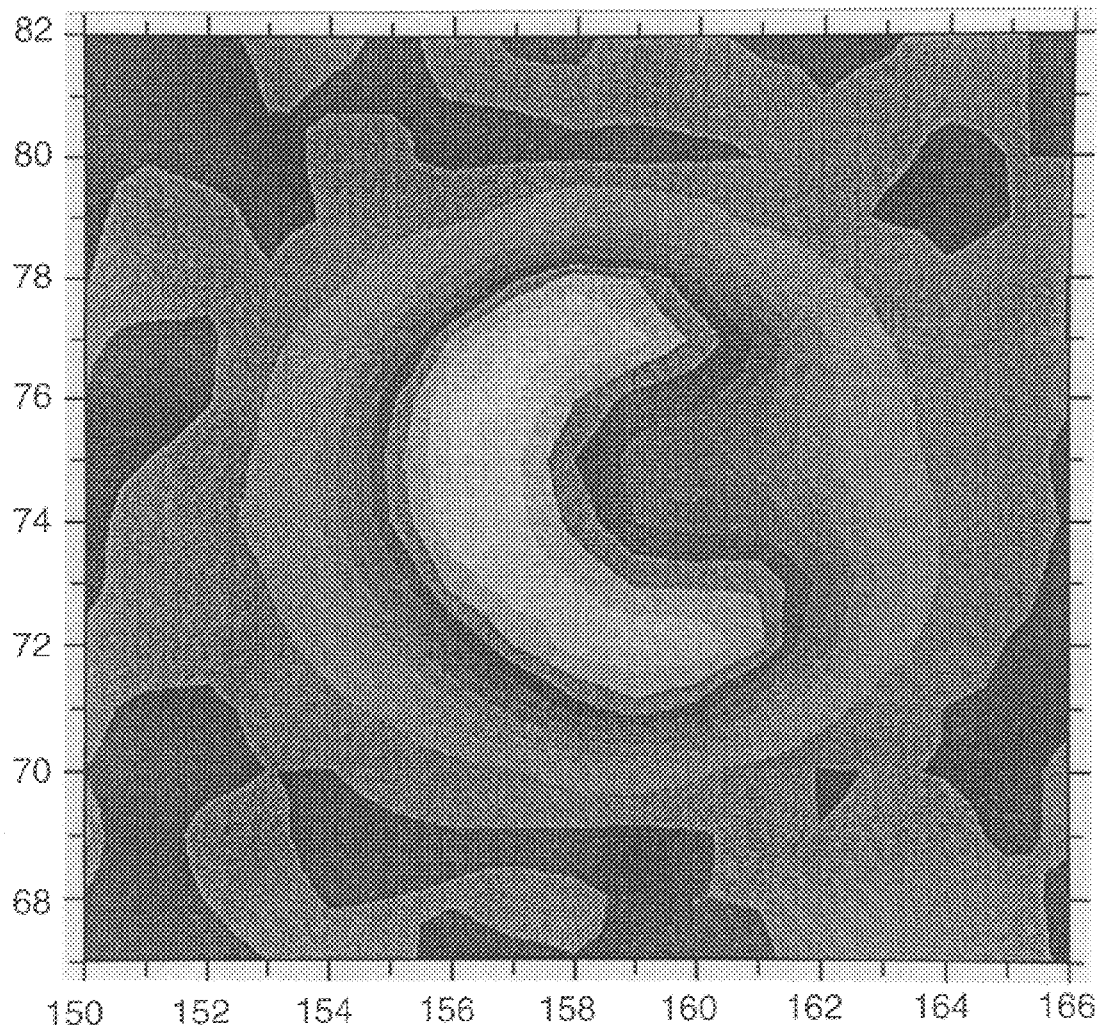
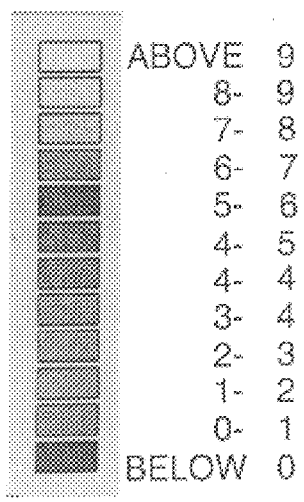
ABOVE 9
8- 9
7- 8
6- 7
5- 6
4- 5
4- 4
3- 4
2- 3
1- 2
0- 1
BELOW 0

FIG. 2
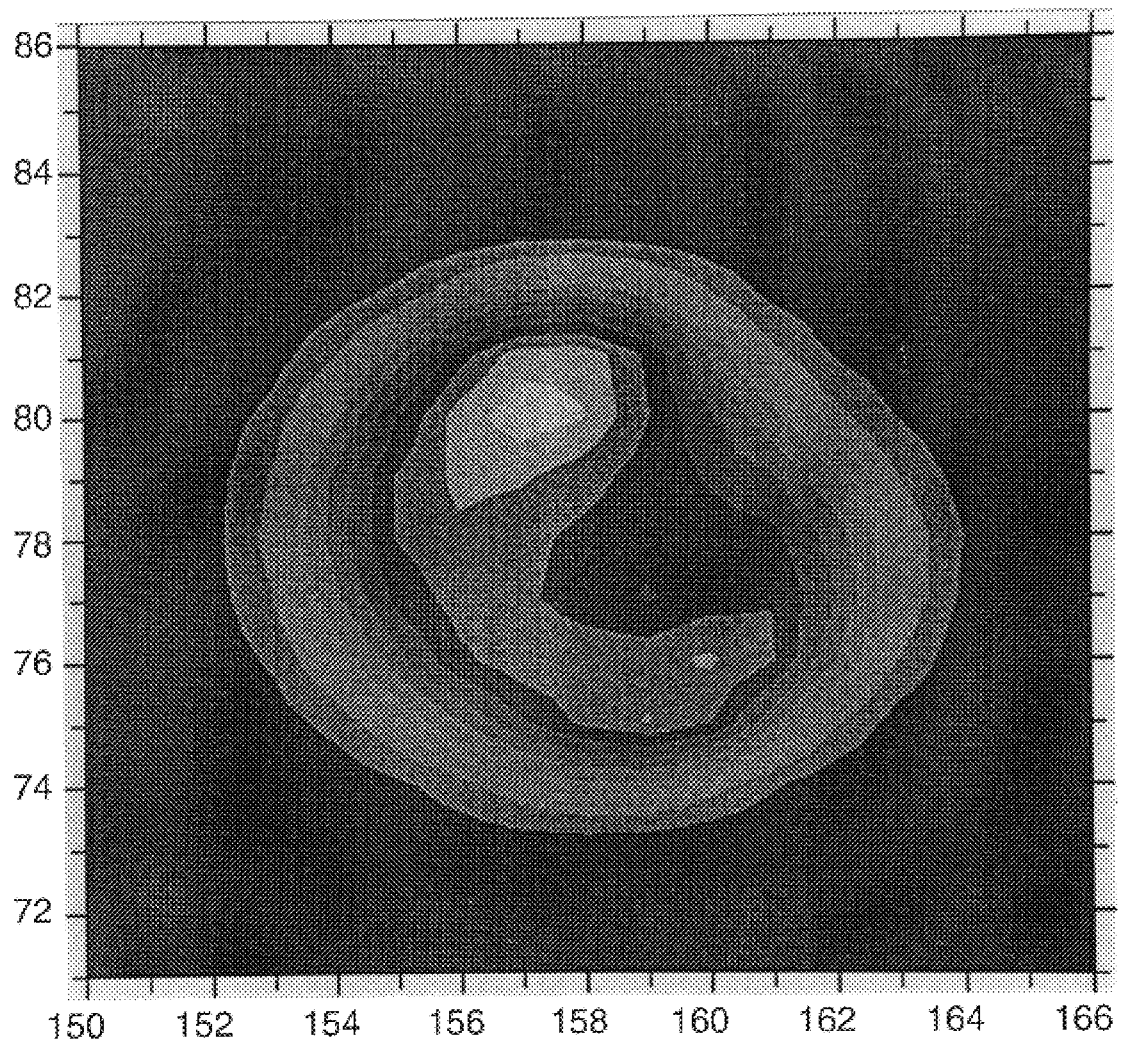
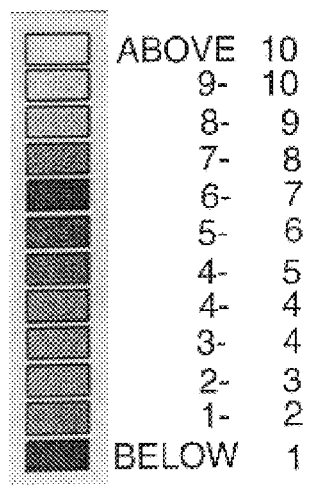

POSTERIOR ANTERIOR SAGGITAL VIEW

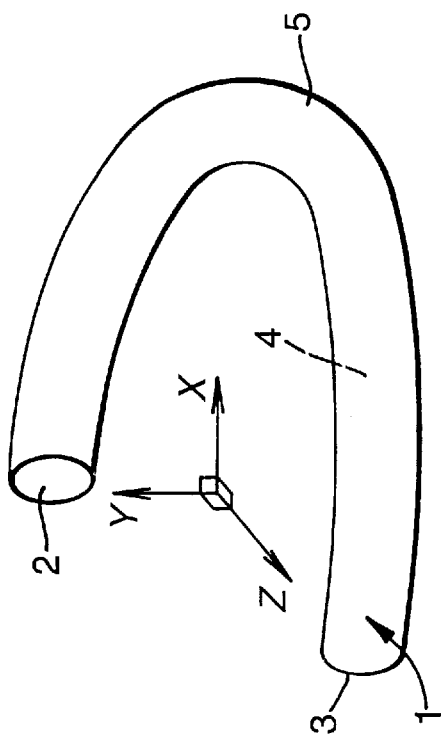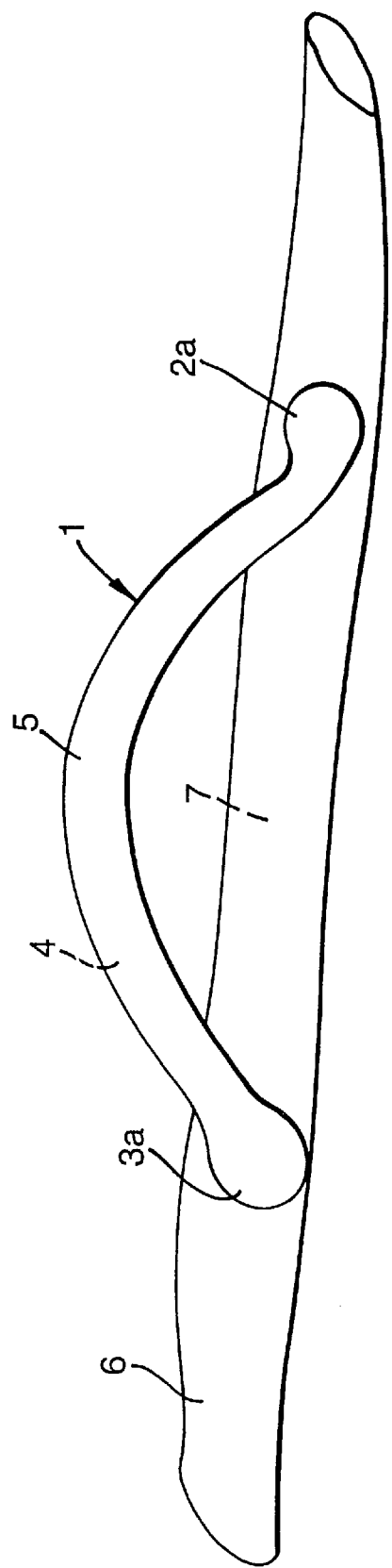

VASCULAR PROSTHESES

BACKGROUND OF THE INVENTION

1. Field of the invention

The arterial system consists largely of curved and branching vessels. Arterial flow is generally laminar but is strongly influenced by inertial forces (Reynolds numbers>>1). Almost all studies of arterial fluid dynamics consider the curvature and branching to be planar. The mechanics of steady flow (Reynolds number>>1) in planar bends and branches are reasonably well understood and involve:

secondary motion in the plane of the bend or bifurcation; low wall shear at the inner wall of the bend (where flow separation may occur) and high wall shear at the outer wall; and low wall shear at the outer wall of a branch (where flow separation may occur) together with high wall shear at the inner wall (flow divider).

2. Description of the Related Art

Several findings indicate that the local blood velocity field influences: (a) the dimensions and mechanical properties of vessels and the morphology, mechanics and metabolism of the endothelium (Yoshida et al, 1988), and (b) the development of vascular disease, in particular atherosclerosis (which causes heart attack and stroke) which develops preferentially in low shear regions in arteries (Yoshida et al, 1988); intimal hyperplasia (which causes the occulusion of vascular grafts) and which develops preferentially in low shear regions in side-to-side veno-arterial bypass grafts (Dobrin et al, 1988; Rittgers and Bhambhani, 1993), and thrombosis which occurs preferentially in low shear regions.

There has been limited consideration in the physiological literature of the mechanics of flow in non-planar bends and branches.

The aortic arch is recognised to curve three-dimensionally and rotational flow has been detected in the aortic arch and descending thoracic aorta (Caro et al, 1971; Frazin et al, 1990).

The branching of the left common coronary artery is recognised to be non-planar and studies in a curved bifurcation model show skewing of the velocity profile away from the 'plane' of bifurcation, both upstream of the bifurcation and in a daughter tube (Batten and Nerem, 1982).

Studies of the velocity field in a realistic model of the abdominal aorta and aortic bifurcation show centrifugal effects caused by the curvature of the abdominal aorta and aortic bifurcation inducing helical flow structures and influencing the localisation of separation zones (Pedersen et al, 1992).

There has been study of the exact anatomical locations of atherosclerotic lesions and of the detailed flow patterns at these locations in transparent isolated human arteries (Asakura and Karino, 1990).

SUMMARY OF THE INVENTION

Recent model experiments by the present inventor led to an investigation as to whether non-planar curvature and branching may be more common than planar curvature and branching in the arterial tree.

With non-planar curvature and branching there is the expectation of skewing of the secondary motion (with the possible development of swirl flow) and alteration of the distribution of wall shear stress from that present with planar curvature and branching. The present inventor has undertaken several studies as a means of determining whether non-planar curvature and branching are common in the circulation. Inspection of a cast of a human aorta and of a rabbit aorta showed the origins of several branches of the aortic arch and abdominal aorta to be tangential to the axis of the parent vessel in more than one plane; non-planar curvature at some bifurcations, for example at the aortic bifurcation; and curvature of the inlet to some bifurcations in a plane other than the 'plane' of bifurcation, as at the lower abdominal aorta.

Phase-shift-based MRI studies have been undertaken with steady laminar flow in a planar model of the aortic bifurcation. When the inlet tube was straight, thin-slice dynamic flow imaging, sensitive to the axial component of the flow, shows the secondary motion in a daughter tube to be in the plane of bifurcation (see FIGS. 1 and 1A). When the inlet tube was curved in a plane normal to the plane of bifurcation, the secondary motion in the daughter tube was skewed (see FIGS. 2 and 2A).

Phase-shift-based MRI studies have also been undertaken on the lower abdominal aorta and aortic bifurcation in healthy human subjects. Cardiac gated projective phase contrast angiograms show the lower abdominal aorta and aortic bifurcation to be curved in a plane normal to the 'plane' of aortic bifurcation (concavity anterior) (FIGS. 3,4). Thin-slice dynamic flow imaging, sensitive to the axial component of the flow, shows skewing of the secondary motion in the common iliac arteries.

Other studies lead to the expectation that the velocity field at the carotid bifurcation is non-planar. Earlier MR studies in healthy human subjects showed the common carotid arteries to be curved in the antero-posterior plane (Caro et al, 1992). Anatomical studies show that the common carotid artery bifurcation does not lie in the antero-posterior plane.

Non-planar curvature and branching have been found to be relatively common in the arterial tree. Non-planar curvature and branching have been found to influence the blood velocity field and may therefore influence vessel biology and the development of vascular disease. From a limited knowledge of vascular bypass surgery, it appears that side-to-side anastomosis, as conventionally performed, involves the construction of a planar bifurcation/confluence (Dobrin et al, 1988; Eastcott, 1992). Side-to-Side anastomoses are prone to fail from intimal hyperplasia, which is associated with low local blood velocity and possibly low local wall shear stress (Dobrin et al, 1988).

In light of these various findings the present invention has been developed.

According to this invention there is provided a vascular prosthesis comprising a length of generally hollow tubing having openings at both ends thereof and including at least one curved portion whose curvature extends within three dimensions of two mutually perpendicular planes such as to induce swirl flow in a liquid medium when such medium flows through said curved portion.

In another aspect we provide a vascular prosthesis comprising at least one hollow body portion from which at least one branch member extends at an intersection between the body portion and said branch member, characterised in that said at least one branch member is of a shape and/or orientation with respect to the body portion such that at least part of said member extends in a non-planar configuration.

At least a section of the said at least one branch member may extend in a plane which is different from that plane of the body portion which includes the central axis of the body portion and the centre of said intersection between body portion and branch member.

Preferably a major part of the branch member may be curved so as to extend at an acute angle with respect to the body portion.

Preferred features of the invention are to be found in the subclaims.

In order that the invention may be illustrated and readily carried into effect, embodiments thereof will now be described by way of example only with reference to the accompanying drawings and wherein:

BRIEF DESCRIPTION OF THE DRAWING

FIG. 1 shows a phase-shifted magnetic resonance image (MRI) of a planar model of aortic bifurcation with straight inlet, mapping the axial velocities in the daughter tube, FIG. 2 shows a similar image map as in FIG. 1, but wherein the inlet tube was curved perpendicularly to the plane of bifurcation, mapping axial velocities also in the daughter tube, FIG. 5 shows one embodiment of a prosthesis including a part helical section, FIG. 6 shows a further embodiment of a suitable prosthetic arterial or venous bypass.

DESCRIPTION OF THE PREFERRED EMBODIMENTS

Figure 1A:
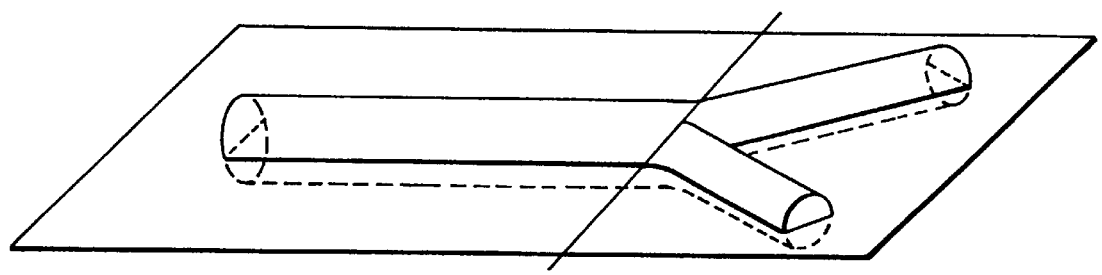
FIG. 1A shows the physical form of the planar model of the aortic bifurcation which produced the image map shown in FIG. 1.

Referring to the drawings, the views of FIGS. 1 to 4 inclusive have already been identified and explained in the introduction hereto.

FIG. 5 shows an embodiment of a prosthesis which comprises a length of generally hollow tubing 1 with openings 2,3 at each end which are adapted for surgical connection to a vein or artery by the provision of suitably shaped flanges. Blood from the circulatory system can flow from inlet 2 to outlet 3 along the hollow interior 4. The curved portion 5 is part helical in that the curvature extends within the X-Z horizontal plane and the mutually perpendicular X-Y plane. Such non planar curvature induces a swirl to the flow to improve circulation and resist the formation of potentially damaging blockages within the interior. The tubing can be made of suitable bio-compatible material and such materials are commercially available and known to those skilled in the art. In order to maintain the tubing open and prevent collapse or kinking it is possible to use a stent or other structural support of plastic, metal or other material internally, externally or integral to the wall of the tubing.

In the FIG. 6 arrangement, showing an arterial (or venous) bypass prosthesis in place, an artery 6 with internal blockage 7 is bypassed by means of a prosthesis according to the invention. The tubing 1 can be of similar shape, size and conformation as that shown in FIG. 1, or the helical proportion can be even shorter in length e.g. less than one half of one turn or revolution. The inlet 2a and outlet 3a flanges have been surgically fastened by stitching to regions of the artery remote from the blockage. Swirl flow is induced by skewing of the blood flow within the non-planar curved portion 5, to improve flow characteristics and reduce the potential for deposit build up.

Figure 7:
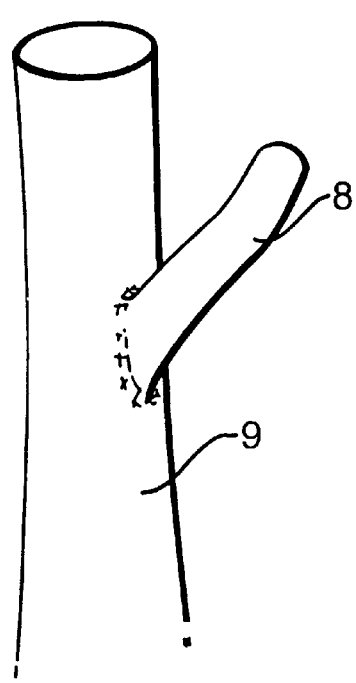
FIGS. 7 and 8 shows an alternative arrangement of prosthetic implant.
Figure 8:
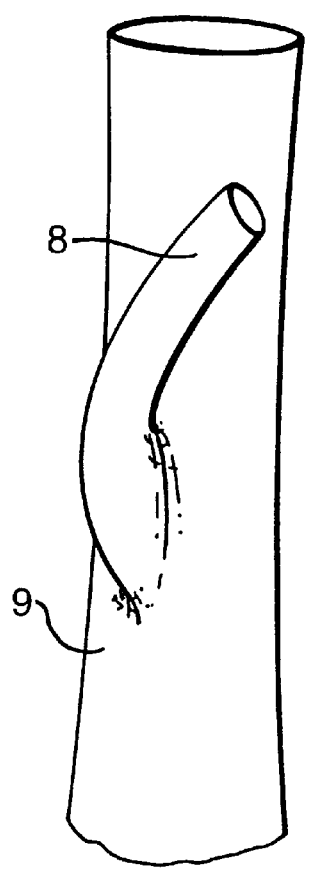

FIGS. 7 and 8 show different arrangements wherein a non planar curved branch member 8 extends from an opening in a hollow body portion 9, which latter may be inserted within a vein or artery either for receiving flow of blood from the said branch member, or for delivering a flow of blood thereto, wherein a swirl flow is established within the non-planar curved branch member.

Figure 9:
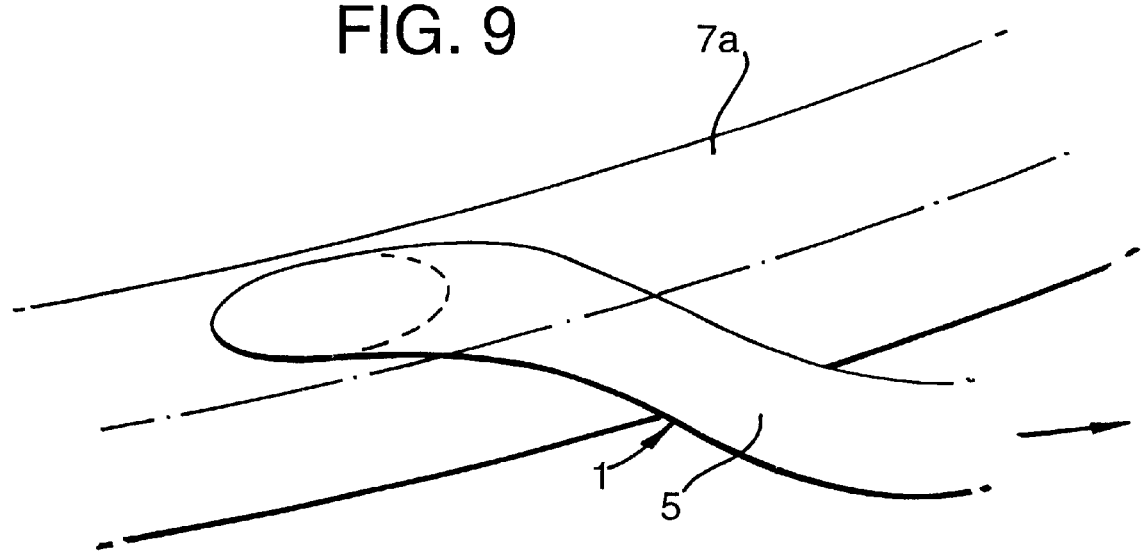
FIG. 9 shows another alternative arrangement of the prosthetic implant.

FIG. 9 shows one form of surgical connection between a prosthesis 1 having spirally curved portion 5 and a blood carrying vessel 7a. The connection between the prosthetic tube 1 and vessel 7a is in the nature of an offset 'plumber's' joint, improving flow to or from the vessel, wherein swirl flow is induced within the prosthesis.

Figure 2A:
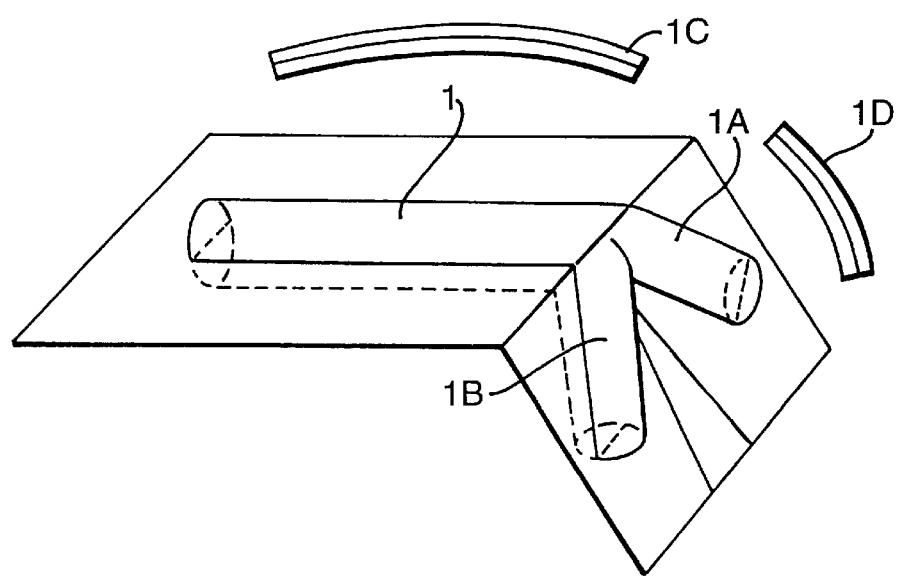
FIG. 2A shows the physical form, including curvilinear variations thereof, of the non-planar model of the aortic bifurcation which produced the image map shown in FIG. 2, and including primary tube 1 or curved tube 1c, daughter tubes 1A and 1B or when curved 1D.
Figure 3:
FIG. 3 shows a cardiac gated projective phase contrast thoracic aorta angiogram, right-left coronal view.
Figure 4:
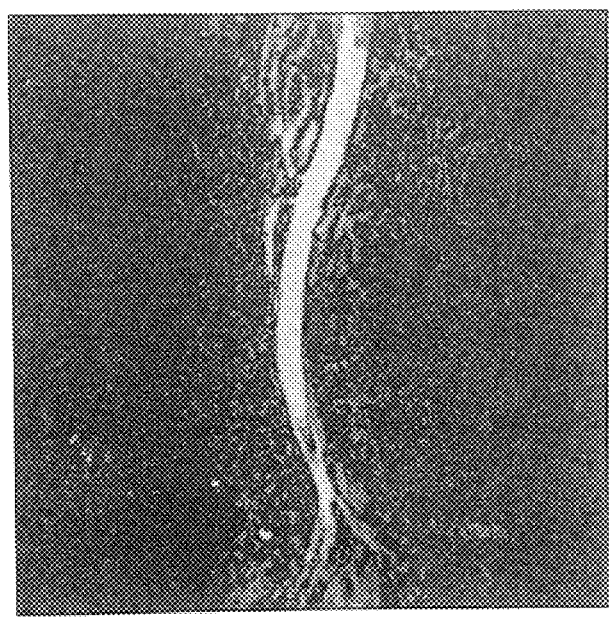
FIG. 4 shows the posterior-anterior saggital view of the angiogram shown in FIG. 3.

Moreover, prosthetic devices according to the invention can include branching such as bifurcation. Indeed an example of a prosthesis is shown in FIG. 2A, particularly including the curved portions 1C and/or 1D.

I claim:

1. A vascular prosthesis comprising a length of generally hollow tubing having openings at both ends thereof, said hollow tubing having at least a portion lying in one of two mutually perpendicular planes, and including at least one curved portion whose curvature extends out of said two mutually perpendicular planes and thereby induces swirl flow in a liquid medium when such medium flows through said curved portion, the vascular prosthesis maintaining its shape prior to implantation.

2. A prosthesis as claimed in claim 1 wherein the ends of the tubing are adapted to permit surgical connection to the vascular system.

3. A prosthesis as claimed in claim 2 wherein the curved portion is part helical in that the length of its curve is less than one complete turn.

4. A prosthesis as claimed in claim 1 wherein the curved portion is part helical in that the length of its curve is less than one complete turn.

5. A prosthesis as claimed in claim 1 which is constructed from a resiliently flexible biocompatible material.

6. A prosthesis as claimed in claim 1 further comprising a structural support which prevents collapse or kinking of the hollow tubing.

7. A prosthesis as claimed in claim 6 wherein the structural support is a stent positioned within the hollow tubing.

8. A vascular prosthesis comprising at least one hollow body portion from which at least one branch member extends at an intersection between the body portion and said branch member, and wherein said at least one branch member is of a shape or orientation with respect to the body portion such that at least part of said branch member extends in a non-planar configuration and thereby induces swirl flow in a liquid medium when such medium flows through said branch member, the vascular prosthesis maintaining its shape prior to implantation.

9. A vascular prosthesis as claimed in claim 8 wherein a section of the said at least one branch member extends in a plane which is different from that plane of the body portion which includes a central axis of the body portion and a centre of said intersection between the body portion and the branch member.

10. A vascular prosthesis as claimed in claim 9 wherein a major part of the branch member may be curved so as to extend at an acute angle with respect to the body portion.

11. A vascular prosthesis as claimed in claim 9 in combination with a vascular joining segment of generally tubular form having a hollow protruberance locatable within an end of said tubing or branch member.

12. A vascular prosthesis as claimed in claim 8 wherein a major part of the branch member may be curved to extend at an acute angle with respect to the body portion.

13. A vascular prosthesis as claim in claim 12 in combination with a vascular joining segment of generally tubular form having a hollow protruberance locatable within an end of said tubing or branch member.

14. A vascular prosthesis as claimed in claim 8 in combination with a vascular joining segment of generally tubular form having a hollow protruberance locatable within an end of said tubing or branch member.

15. A vascular prosthesis as claimed in claim 8 further comprising a structural support which prevents collapse or kinking of the vascular prosthesis.

16. A vascular prosthesis as claimed in claim 15 wherein the structural support is a stent positioned within the vascular prosthesis.

17. A vascular prosthesis comprising:
   a hollow body portion having openings at opposite ends adapted to permit surgical connection to the vascular system;
   a tubular branch member extending from the hollow body portion at an intersection and having an end adapted to permit surgical connection to the vascular system;
   a plane of the body portion including a central axis of the body portion and a center point of the intersection; and
   wherein said branch member extends in a plane which is different from the plane of the body portion and thereby induces swirl flow in a liquid medium when such medium flows through said branch member, the vascular prosthesis maintaining its shape prior to implantation.

18. A vascular prosthesis as claimed in claim 17 wherein a major portion of the branch member is curved in a part helical shape.

19. A vascular prosthesis comprising a length of generally hollow tubing having openings at both ends thereof, said hollow tubing having at least a portion lying in a first plane, and including at least one curved portion which is at least part helical in that its curvature is non planar and thereby induces swirl flow in a liquid medium when such medium flows through said curved portion.

* * * * *